(12) United States Patent
Hadjicostis

(10) Patent No.: US 11,109,909 B1
(45) Date of Patent: Sep. 7, 2021

(54) IMAGE GUIDED INTRAVASCULAR THERAPY CATHETER UTILIZING A THIN ABLATION ELECTRODE

(71) Applicant: Andreas Hadjicostis, McKinney, TX (US)

(72) Inventor: Andreas Hadjicostis, McKinney, TX (US)

( * ) Notice: Subject to any disclaimer, the term of this patent is extended or adjusted under 35 U.S.C. 154(b) by 85 days.

(21) Appl. No.: 16/700,185

(22) Filed: Dec. 2, 2019

Related U.S. Application Data

(63) Continuation-in-part of application No. 16/259,740, filed on Jan. 28, 2019, now Pat. No. 10,492,760, which is a continuation-in-part of application No. 15/633,716, filed on Jun. 26, 2017, now Pat. No. 10,188,368.

(51) Int. Cl.
| | | |
|---|---|---|
| A61B 18/14 | (2006.01) | |
| A61B 8/12 | (2006.01) | |
| G02B 27/09 | (2006.01) | |
| G10K 11/30 | (2006.01) | |
| A61M 25/01 | (2006.01) | |
| G02B 1/04 | (2006.01) | |
| A61B 18/00 | (2006.01) | |

(52) U.S. Cl.
CPC ............ *A61B 18/1492* (2013.01); *A61B 8/12* (2013.01); *A61M 25/01* (2013.01); *G02B 1/04* (2013.01); *G02B 27/0983* (2013.01); *G10K 11/30* (2013.01); *A61B 2018/00345* (2013.01); *A61B 2018/00577* (2013.01); *A61M 2025/0166* (2013.01)

(58) Field of Classification Search
CPC .................. A61B 18/1492; A61B 8/12; A61B 2018/00577; A61B 2018/00345; G10K 11/30; G02B 27/0983; G02B 1/04; A61M 25/01; A61M 2025/0166
See application file for complete search history.

(56) References Cited

U.S. PATENT DOCUMENTS

| | | | |
|---|---|---|---|
| 3,827,115 | A | 8/1974 | Bom |
| 3,938,502 | A | 2/1976 | Bom |
| 4,446,395 | A | 5/1984 | Hadjicostis |
| 4,532,924 | A | 8/1985 | Auth et al. |
| 4,643,186 | A | 2/1987 | Rosen et al. |

(Continued)

FOREIGN PATENT DOCUMENTS

| | | |
|---|---|---|
| CN | 106037803 A | 10/2016 |
| EP | 1717601 | 2/2008 |

(Continued)

OTHER PUBLICATIONS

Hackler, et al., Semiconductor-on-Polymer Wafer Level Chip Scale Packaging.

*Primary Examiner* — Sanjay Cattungal
(74) *Attorney, Agent, or Firm* — Timothy E. Siegel Patent Law, PLLC; Timothy E. Siegel

(57) ABSTRACT

A method of forming a sound lens having a coating of a first metal, that utilizes a lens-shaped piece of heat resistant material, having a convex major surface, and having a sonic impedance similar to that of human tissue, taken from a group consisting essentially of high temperature plastics and silicone. In the method, the convex major surface is sputter coated with a layer of the first metal, less than 10 microns thick.

4 Claims, 11 Drawing Sheets

(56) References Cited

U.S. PATENT DOCUMENTS

| | | | |
|---|---|---|---|
| 4,682,596 | A | 7/1987 | Bales et al. |
| 4,725,989 | A * | 2/1988 | Granz .................... G10K 11/26 |
| | | | 367/13 |
| 4,794,931 | A | 1/1989 | Yock |
| 4,939,826 | A | 7/1990 | Schoup |
| 5,009,232 | A * | 4/1991 | Hassler .............. A61B 17/2256 |
| | | | 600/439 |
| 5,010,886 | A | 4/1991 | Passafaro et al. |
| 5,098,431 | A | 3/1992 | Rydell |
| 5,159,931 | A | 11/1992 | Pini |
| 5,176,141 | A | 1/1993 | Bom et al. |
| 5,240,003 | A | 8/1993 | Lancee et al. |
| 5,269,292 | A * | 12/1993 | Granz ................. A61B 17/2258 |
| | | | 367/150 |
| 5,291,893 | A | 3/1994 | Slayton |
| 5,317,229 | A * | 5/1994 | Koehler ................ B06B 1/0611 |
| | | | 310/317 |
| 5,327,905 | A | 7/1994 | Avitall |
| 5,359,760 | A | 11/1994 | Busse et al. |
| 5,425,364 | A | 6/1995 | Imran |
| 5,454,809 | A | 10/1995 | Janssen |
| 5,592,730 | A | 1/1997 | Greenstein et al. |
| 5,622,177 | A | 4/1997 | Breimesser et al. |
| 5,626,576 | A | 5/1997 | Janssen |
| 5,749,914 | A | 5/1998 | Janssen |
| 5,771,895 | A | 6/1998 | Slager |
| 5,788,636 | A | 8/1998 | Curley |
| 5,840,030 | A | 11/1998 | Ferek-Petric et al. |
| 5,840,031 | A | 11/1998 | Crowley |
| 5,857,974 | A | 1/1999 | Eberle et al. |
| 5,893,832 | A | 4/1999 | Song |
| 5,924,993 | A | 7/1999 | Hadjicostis et al. |
| 5,935,108 | A | 8/1999 | Kathoh et al. |
| 6,004,269 | A * | 12/1999 | Crowley .............. A61B 8/4461 |
| | | | 600/374 |
| 6,047,216 | A | 4/2000 | Carl et al. |
| 6,066,096 | A | 5/2000 | Smith et al. |
| 6,099,524 | A | 8/2000 | Lipson et al. |
| 6,356,790 | B1 | 3/2002 | Maguire et al. |
| 6,394,956 | B1 | 5/2002 | Chandrasekaran et al. |
| 6,560,472 | B2 | 5/2003 | Hill et al. |
| 6,572,551 | B1 | 6/2003 | Smith et al. |
| 6,582,369 | B1 | 6/2003 | Huang et al. |
| 6,582,423 | B1 | 6/2003 | Thapliyal |
| 6,679,845 | B2 | 1/2004 | Ritter et al. |
| 6,709,396 | B2 | 3/2004 | Flesch et al. |
| 6,783,497 | B2 | 8/2004 | Grenon et al. |
| 6,852,109 | B2 | 2/2005 | Winston et al. |
| 6,858,006 | B2 | 2/2005 | MacCarter et al. |
| 6,892,438 | B1 | 5/2005 | Hill et al. |
| 6,899,682 | B2 | 5/2005 | Eberle et al. |
| 6,925,693 | B2 | 8/2005 | Takeuchi et al. |
| 6,962,567 | B2 | 11/2005 | Eberle et al. |
| 6,972,018 | B2 | 12/2005 | Ryan et al. |
| 6,994,674 | B2 | 2/2006 | Sheljaskow et al. |
| 7,004,940 | B2 | 2/2006 | Ryan et al. |
| 7,022,088 | B2 | 4/2006 | Keast et al. |
| 7,045,108 | B2 | 5/2006 | Jiang et al. |
| 7,053,530 | B2 | 5/2006 | Baumgartner et al. |
| 7,060,033 | B2 | 6/2006 | White et al. |
| 7,066,895 | B2 | 6/2006 | Podany |
| 7,074,218 | B2 | 7/2006 | Washington et al. |
| 7,112,196 | B2 | 9/2006 | Brosch et al. |
| 7,115,092 | B2 | 10/2006 | Park et al. |
| 7,156,812 | B2 | 1/2007 | seward et al. |
| 7,156,938 | B2 | 1/2007 | Baumgartner et al. |
| 7,195,179 | B2 | 3/2007 | miller et al. |
| 7,226,417 | B1 | 6/2007 | Eberle |
| 7,519,410 | B2 | 4/2009 | Taimisto et al. |
| 7,596,415 | B2 | 9/2009 | Brabec et al. |
| 7,844,347 | B2 | 11/2010 | Brabec et al. |
| 8,414,492 | B2 | 4/2013 | Hadjicostis |
| 8,425,421 | B2 | 4/2013 | Hadjicostis |
| 8,702,609 | B2 | 4/2014 | Hadjicostis |
| 8,974,446 | B2 | 3/2015 | Nguyen et al. |
| 9,138,290 | B2 | 9/2015 | Hadjicostis |
| 9,307,953 | B2 | 4/2016 | Lee et al. |
| 10,405,828 | B2 * | 9/2019 | Deladi .................... B06B 1/0629 |
| 10,492,760 | B2 | 12/2019 | Hadjicostis |
| 2003/0028107 | A1 * | 2/2003 | Miller ...................... A61B 8/12 |
| | | | 600/437 |
| 2003/0055308 | A1 | 3/2003 | Freimel et al. |
| 2004/0068191 | A1 | 4/2004 | Seward |
| 2004/0073118 | A1 * | 4/2004 | Peszynski ................ A61B 8/12 |
| | | | 600/459 |
| 2004/0092806 | A1 | 5/2004 | Sagon et al. |
| 2004/0147920 | A1 | 7/2004 | Keidar |
| 2004/0254471 | A1 | 12/2004 | Hadjicostis |
| 2004/0254570 | A1 | 12/2004 | Hadjicostis et al. |
| 2005/0033182 | A1 | 2/2005 | Cerofolini |
| 2005/0085731 | A1 * | 4/2005 | Miller ...................... A61B 8/12 |
| | | | 600/459 |
| 2005/0107783 | A1 | 5/2005 | Tom et al. |
| 2005/0159739 | A1 | 7/2005 | Paul et al. |
| 2005/0228290 | A1 | 10/2005 | Borovsky |
| 2005/0251127 | A1 | 11/2005 | Brosch et al. |
| 2006/0030844 | A1 | 2/2006 | Knight et al. |
| 2007/0016068 | A1 * | 1/2007 | Grunwald ................ A61B 8/12 |
| | | | 600/468 |
| 2007/0167804 | A1 | 7/2007 | Park et al. |
| 2007/0189761 | A1 | 8/2007 | Sudol |
| 2007/0246821 | A1 | 10/2007 | Lu et al. |
| 2008/0200815 | A1 | 8/2008 | Van Der Steen |
| 2008/0214938 | A1 * | 9/2008 | Solomon ................ A61B 8/546 |
| | | | 600/459 |
| 2008/0312536 | A1 | 12/2008 | Dala-Krishna |
| 2011/0071395 | A1 * | 3/2011 | Miller .................. G01S 15/8925 |
| | | | 600/439 |
| 2012/0245469 | A1 * | 9/2012 | McGee ................... A61B 5/283 |
| | | | 600/447 |
| 2012/0265069 | A1 * | 10/2012 | Sliwa ...................... A61B 8/12 |
| | | | 600/439 |
| 2012/0265192 | A1 * | 10/2012 | Sliwa .................... A61B 8/5223 |
| | | | 606/33 |
| 2013/0230930 | A2 * | 9/2013 | VanDoorn ................ G01N 1/44 |
| | | | 436/174 |
| 2013/0267853 | A1 | 10/2013 | Dausch et al. |
| 2013/0301380 | A1 * | 11/2013 | Oraevsky ............. A61B 8/5261 |
| | | | 367/7 |
| 2014/0005706 | A1 * | 1/2014 | Gelfand ............. A61B 17/2202 |
| | | | 606/169 |
| 2014/0180101 | A1 | 6/2014 | Hadjicostis |
| 2015/0099976 | A1 | 4/2015 | Ghaffari et al. |
| 2016/0008067 | A1 | 1/2016 | Hadjicostis |
| 2016/0113633 | A1 | 4/2016 | Hadjicostis |
| 2016/0249859 | A1 * | 9/2016 | Babkin .................... A61B 5/339 |
| | | | 600/509 |
| 2016/0374710 | A1 * | 12/2016 | Sinelnikov ............. A61B 8/481 |
| | | | 600/439 |
| 2017/0136496 | A1 * | 5/2017 | Jacobs .................... H01L 21/78 |
| 2018/0368805 | A1 | 12/2018 | Hadjicostis |

FOREIGN PATENT DOCUMENTS

| | | |
|---|---|---|
| EP | 2136603 | 12/2009 |
| JP | H02134149 A | 5/1990 |
| JP | H02140156 A | 5/1990 |
| KR | 20060112244 | 10/2006 |
| WO | 9519143 | 7/1995 |
| WO | 9745157 A1 | 12/1997 |
| WO | 9912489 | 3/1999 |

* cited by examiner

IMAGE GUIDED INTRAVASCULAR THERAPY CATHETER UTILIZING A THIN ABLATION ELECTRODE

RELATED APPLICATIONS

This application is a continuation-in-part of U.S. patent application Ser. No. 16/259,740, filed Jan. 28, 2019, which itself is a continuation-in-part of U.S. patent application Ser. No. 15/633,716, filed Jun. 26, 2017, now U.S. Pat. No. 10,188,368, issued Jan. 29, 2019, both of which are incorporated by reference as if fully set forth herein.

BACKGROUND

U.S. Pat. No. 8,702,609, which is assigned to the assignee of the present application, discloses an image guided— therapy catheter that uses ultrasound to form an image of the interior of a blood vessel directly in front of the catheter, to determine the locations of plaque, and then permits the use of this information in driving a set of RF ablation electrodes to selectively ablate plaque, while avoiding damaging the interior surfaces of the blood vessel. A number of challenging issues are presented in the design of this type of device. Among these is the acoustic characteristics of the medical device and how to avoid harmful interference to the returning signal from signal that has reflected from the portion of the device proximal (that is, further back from the tip) to the ultrasound array.

Another troublesome issue in the design of the system is the multiplexing of the driving/receiving coax lines for the ultrasound elements. With a large array, it would be impossible to have a separate coax line for each element. Multiplexors, however, require an increasing number of control inputs for an increasing number of multiplexed lines. With catheter space at an extreme premium, fitting a high number of control lines into a catheter is also very problematic.

Although having a large array that gathers a great quantity of data permits high-quality 3D imagery, it can also slow down the frame rate. In some instances a surgeon may desire a faster frame rate.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of an endoluminal catheter for providing image-guided therapy in a patient's vasculature, having an elongated catheter body adapted to be inserted into a patient's vasculature, the catheter body defining a distal portion operable to be inside the patient's vasculature while a proximal portion is outside the patient. A distal element includes a sound lens having a distal surface and a set of electrodes adhered to the sound lens distal surface and forming a convex, generally round distal facing catheter face, defining a radial center, and bearing separately-controllable electrodes for performing controlled ablation of plaque in the patient's vasculature, each electrode extending away from the radial center in a direction different from the other electrodes. Also, a distal facing array of ultrasound imaging transducers is positioned in the catheter body proximal to the electrodes and configured to transmit and receive ultrasound pulses through the electrodes to provide real time imaging information of plaque to be ablated by the electrodes. Accordingly, a catheter operator can form an image of plaque on an artery interior and in response selectively activate one or more electrodes to remove plaque along a first circumferential portion of an arterial wall, while avoiding activating an electrode along a circumferential portion of an arterial wall that does not bear plaque. Finally, the electrodes are less than 10 microns thick.

In a second separate aspect, the present invention may take the form of a method of forming a sound lens having a coating of a first metal, that utilizes a lens-shaped piece of heat resistant material, having a convex major surface, and having a sonic impedance similar to that of human tissue, taken from a group consisting essentially of high temperature plastics and silicone. In the method, the convex major surface is sputter coated with a layer of the first metal, less than 10 microns thick.

In a third separate aspect, the present invention may take the form of a method of forming a sound lens having a surface of a target convex shape and having a coating of a first metal and which utilizes a foil of the first metal, thinner than 10 microns thick. In the method the foil is pressed into a mold having a concave shape reverse to the target convex shape. Then, a material in a melt state, taken from a group consisting of high temperature castable silicone elastomers, is poured into the foil and cured. Finally, the cured material and foil are removed from the mold.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
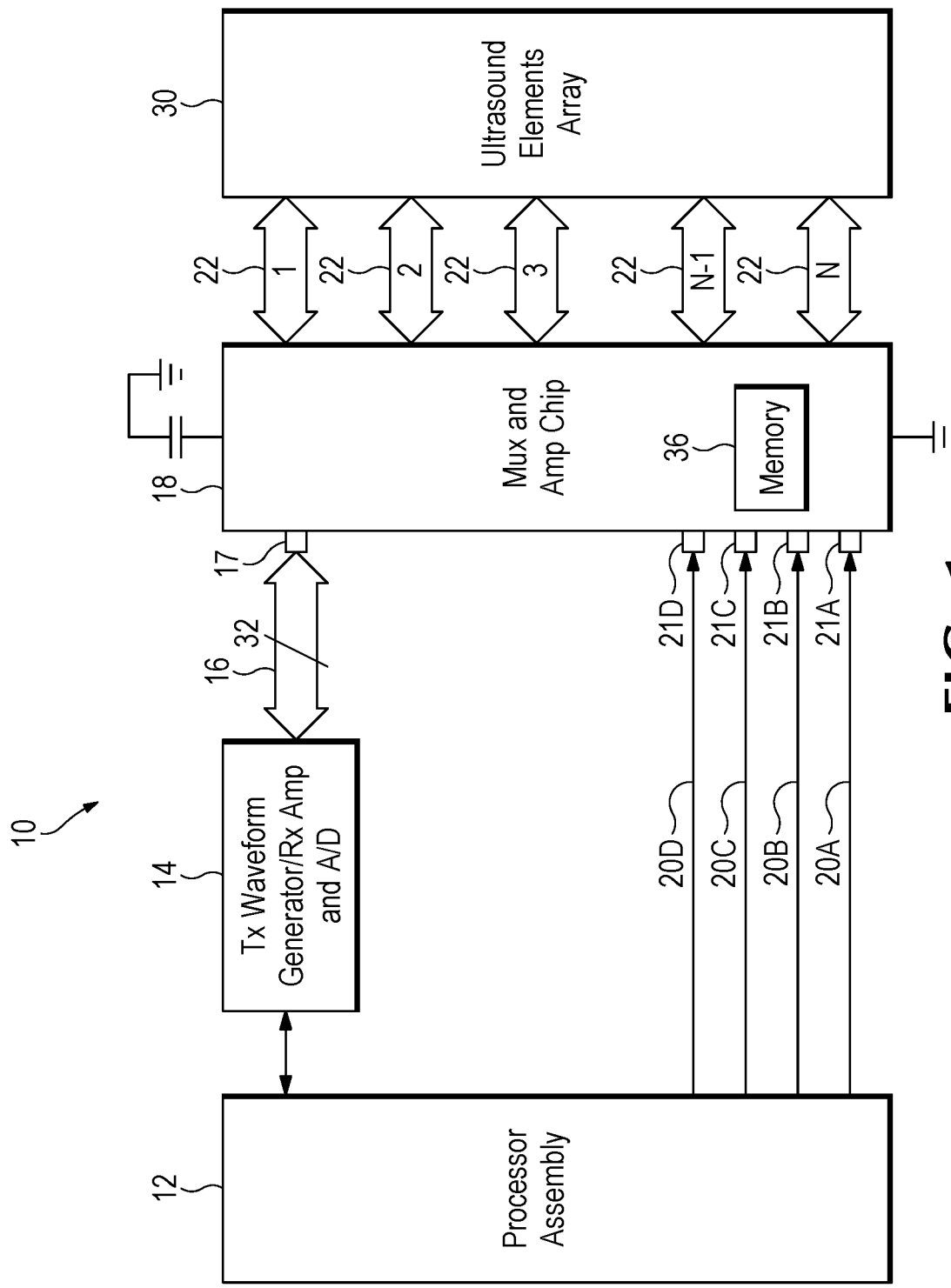
FIG. 1 is a block diagram of the ultrasound system of a medical device, according to the present invention.
Figure 2:
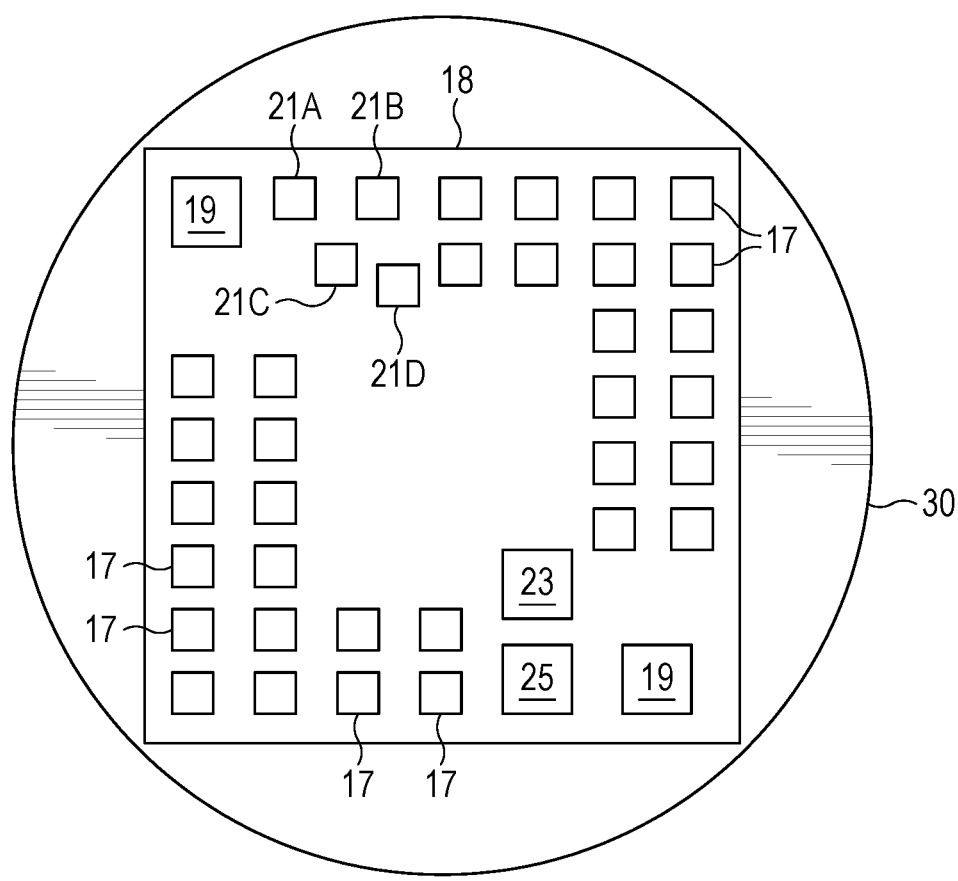
FIG. 2 is a physical representation of the proximal side of the mux and amp chip shown in block form in FIG. 1.
Figure 3:
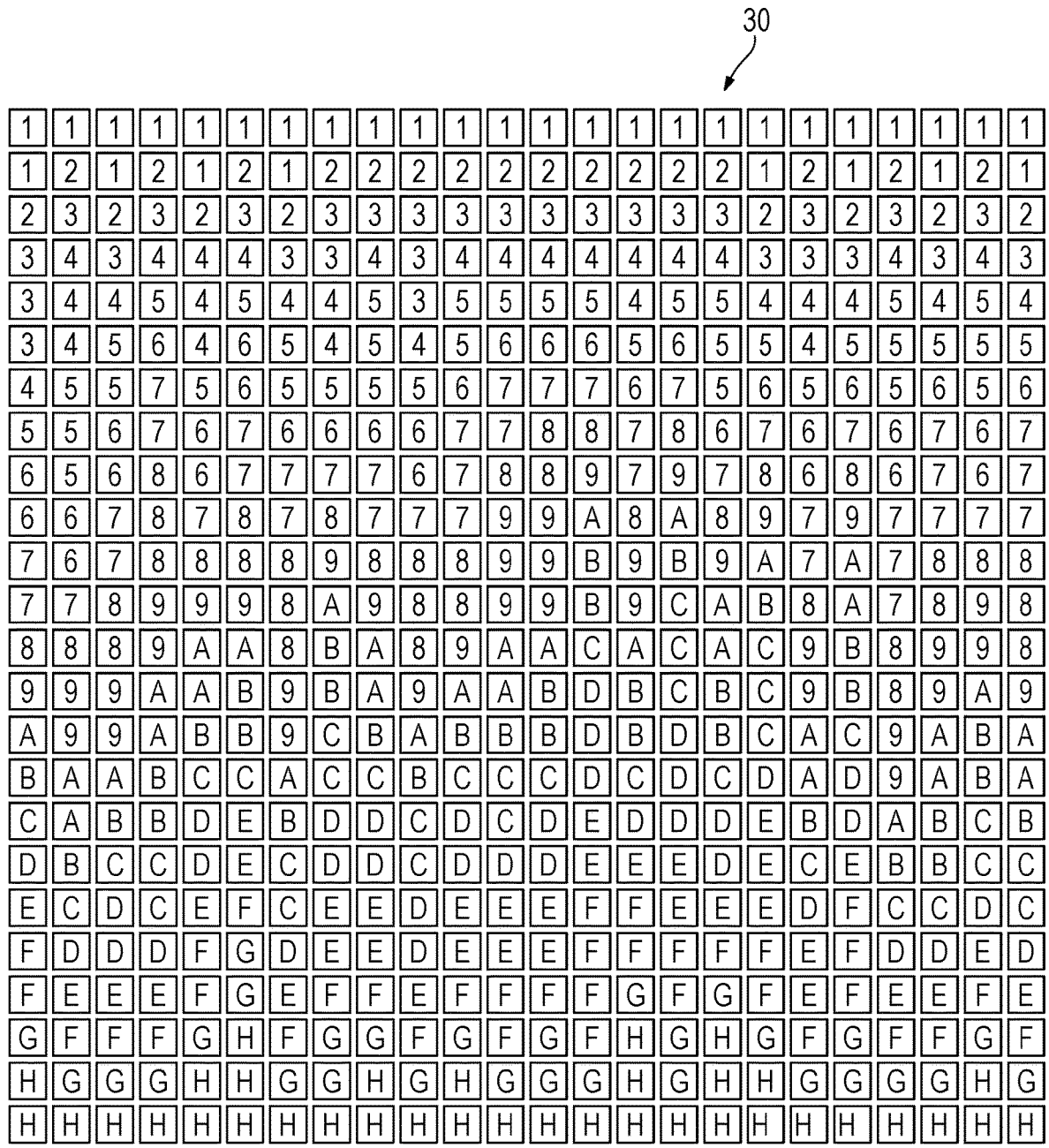
FIG. 3 is a proximal side view of the elements of the ultrasound array, shown in block form in FIG. 1, showing one allocation of ultrasound elements into eighteen blocks 1 through H.
Figure 4:
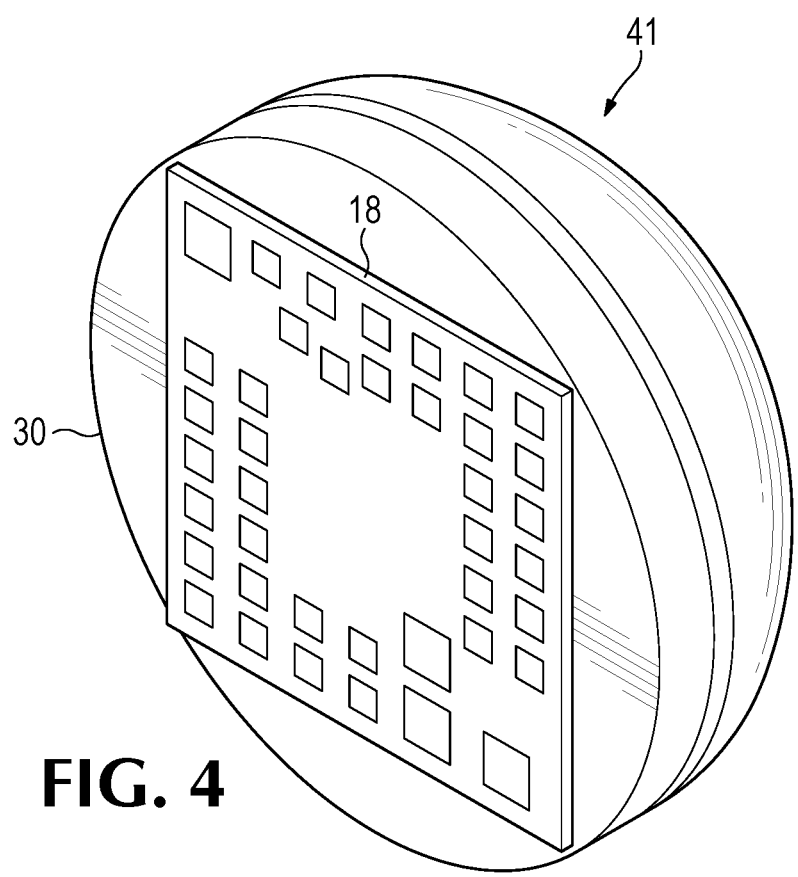
FIG. 4 is a side rear isometric view of the imaging head of the system of FIG. 1.
Figure 5:
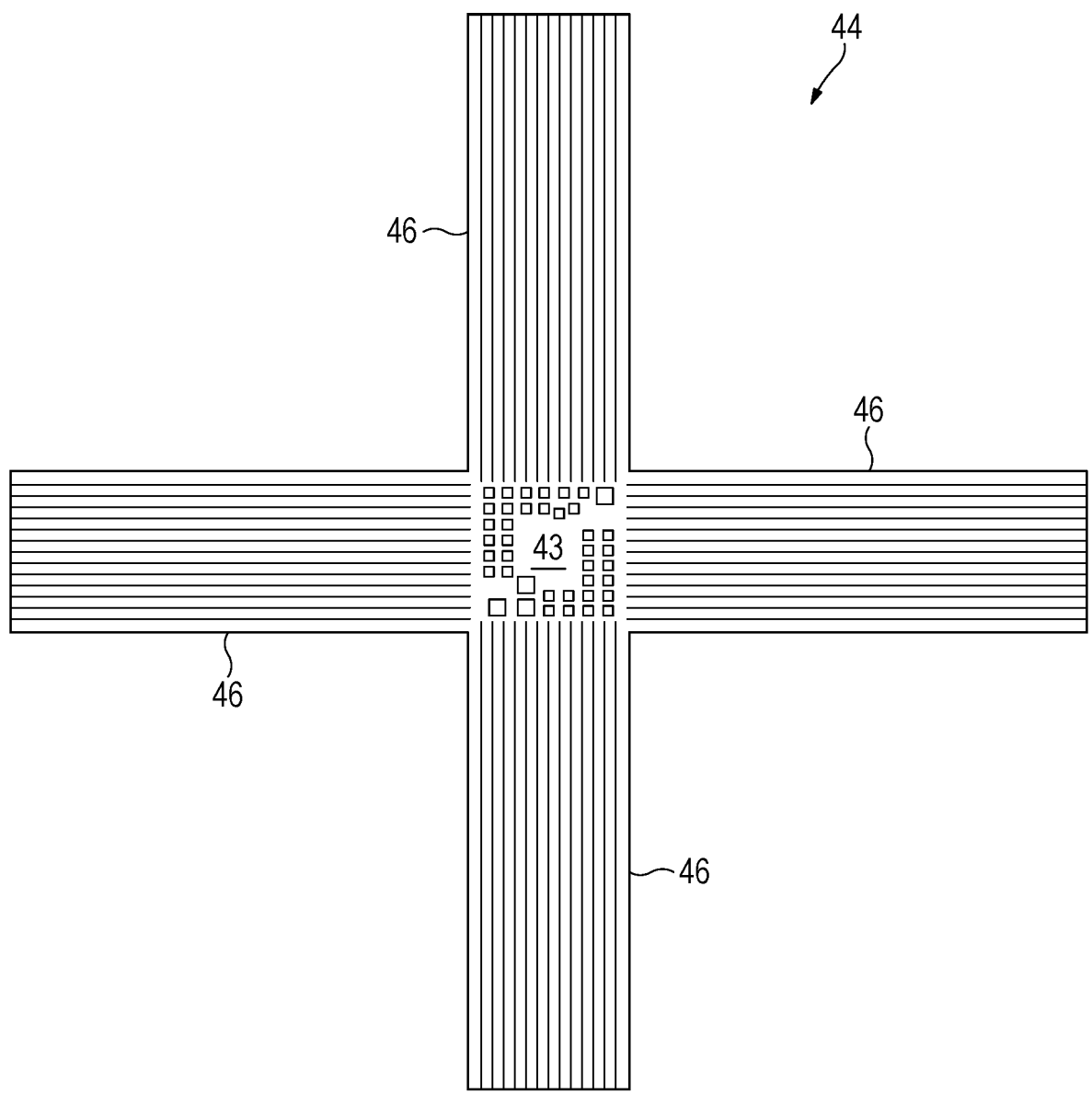
FIG. 5 is a view of an article of flex circuit used in the system of FIG. 1.
Figure 6:
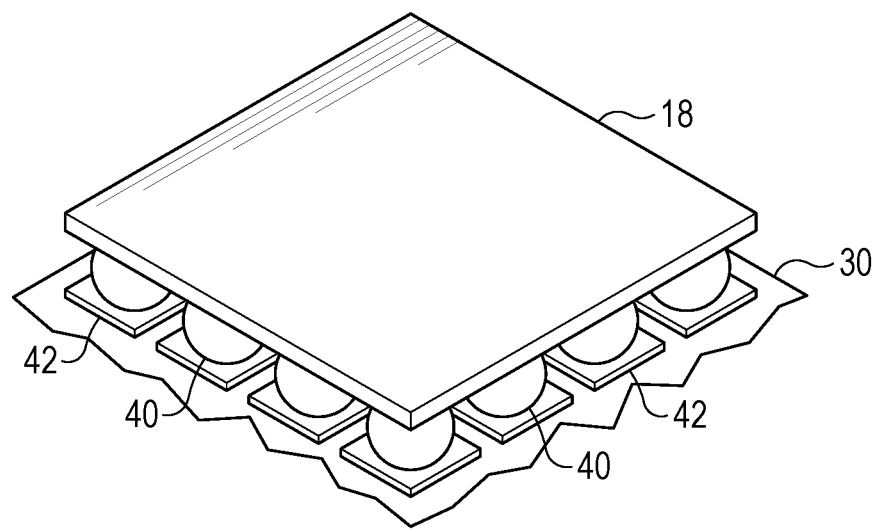
FIG. 6 is an illustration of the flip chip technique which may be used as a step in the production of the imaging head of FIG. 5.
Figure 7:
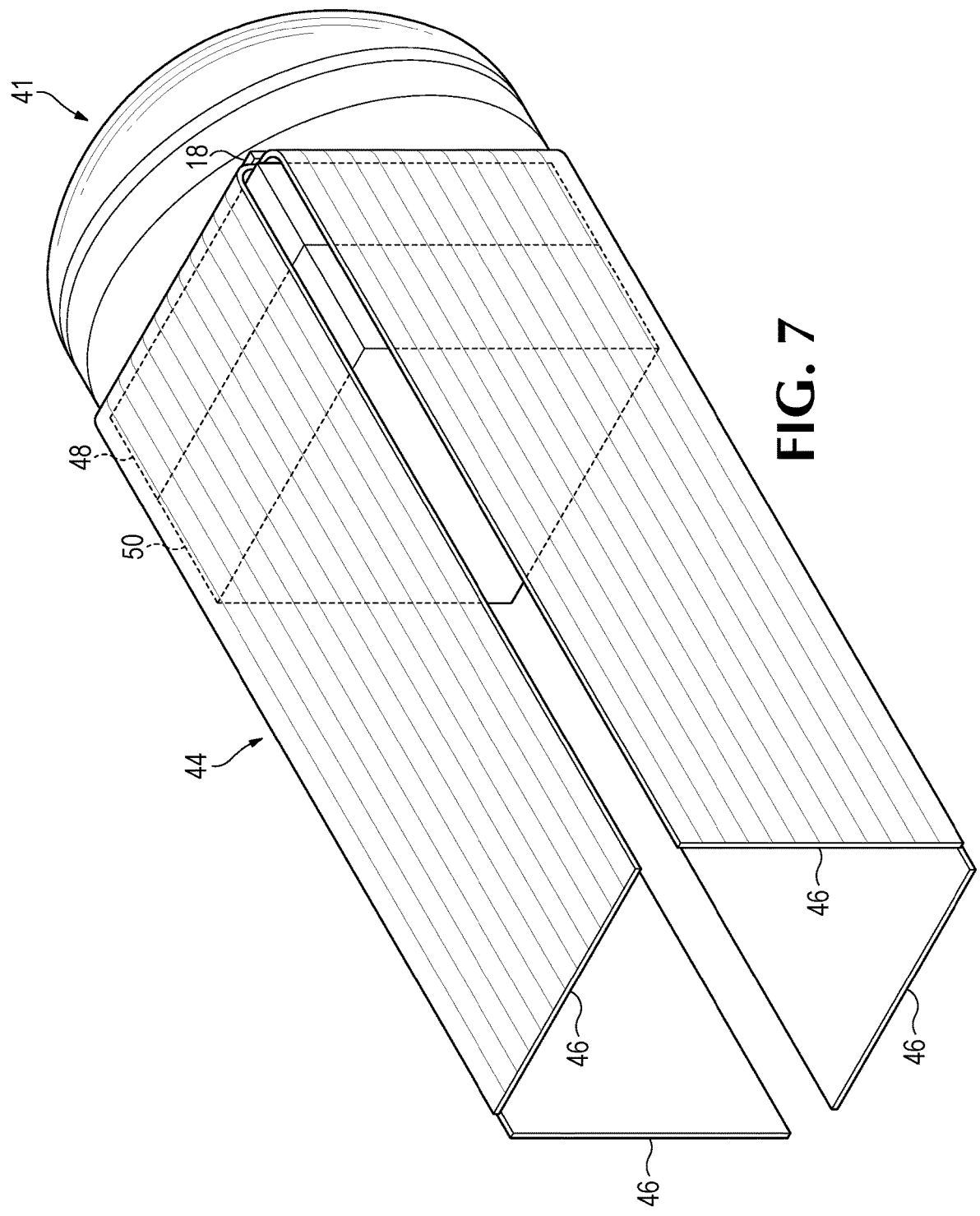
FIG. 7 is a side rear isometric view of the imaging head of FIG. 5, shown including further proximal elements.

Referring to FIGS. 1 and 2, in a first preferred embodiment of an ultrasound imaging system 10, having a distal portion housed in a catheter sized to enter cardiac arteries, a processor assembly 12 commands a waveform signal generating network 14, which generates 35 MHz waveforms for 32 coax signal lines 16, which drive and receive from a set of 32 input/output contacts 17, on an integrated circuit die (henceforth "multiplexor chip" or "chip") 18. In one preferred embodiment, multiplexor chip 18 is less than 12 µm in thickness. In alternative embodiments, chip 18 is less than 20, 40, 60 and 80 µm. Control lines 20A-20D extend from processor 12 to multiplexor 18, attaching to contact pads 21A-21D, respectively, and must command multiplexor 18, for each phase to switch the 32 signal lines 16 to a one out of a set of 18 designated blocks 22 of drive/sense contacts, to drive one out of eighteen blocks of thirty-two ultrasound elements in a 24×24 (576) ultrasound element array 30. In a preferred embodiment array 30 is made of a piezoelectric material, such as a piezoelectric ceramic. It is possible that at some point another technology, such as capacitive micromachined ultrasound transducers (CMUT) may be usable in this application. Thirty-two micro-coax lines are required for the input/output contacts 17 with the grounds tied together and then eventually to a common ground (analog ground 19) on the chip 18. Plus, four more wires are required for digital or logic control and power to the IC chip 18. In addition, in one embodiment four wires are required to transmit the RF signals to RF ablation electrodes (noted below). These wires physically bypass chip 18.

The basic function of the chip 18 is to allow 32 micro-coax acoustic channels to selectively connect to any group of thirty-two ultrasound array elements and to amplify the return and filter signals from the ultrasound elements, as they are transmitted to the coax signal lines 16. On power-up the ultrasound system resets the chip 18 and asserts the Tx/Rx line placing the MUX in transmit mode for elements 1-32. The ultrasound system then transmits an electrical analog pulse through each of the micro-coax cables to contacts 17. The electrical pulses are then transferred to elements 1-32 of the piezoelectric array. After the ultrasonic pulses have left elements 1-32, the Tx/Rx line is de-asserted placing the MUX in receive mode. In the receive mode mechanical energy reflected from the tissue or blood is converted to electrical energy by the piezoelectric elements 1-32 and the power transferred back through the chip 18 where the signal is amplified (using power received on contact pad 23), bandpass filtered and matched to the cable and sent back through each micro-coax to the ultrasound system for conversion to digital data at the front end of the imaging system. In a preferred embodiment the band pass filtering takes the form of a third order Butterworth band pass in the frequency range of 20 to 50 MHz. The Receive mode lasts for approximately 8 µS. Tx/Rx is then re-asserted and the cycle repeats for element 33-64 and so forth. A chip ground 25 is electrically connected to a further ground at the proximal end of a linear conductor.

During the transmit cycle the input electrical impedance of the IC chip 18 on the flex side of the chip 18 is matched to that of the coaxial cable (typically 50 to 100 Ohm characteristic impedance), whereas the output impedance of the IC chip 18 is matched, or optimized, to the electrical impedance of the individual piezoelectric elements of the array (typically 10,000 Ohms). The electrical impedance matching scheme works also in the receive cycle to enable optimal transmission of power. In summary the IC chip 18 performs multiple functions in the operation of the imaging system: It enables the electrical connection of multiple micro-coaxial cables to the individual elements of the array, it matches the electrical impedance of the coaxial cables to that of the piezoelectric elements, it acts as multiplexer so the entire array of elements can be addressed, acts as an amplifier of the weak receive signals (of the order of a few microvolts) in receive mode, and also as an electronic filter that allows only a certain range of frequencies to pass through in receive mode.

In one scheme of driving the ultrasound array 30, the following transmit receive sequence is performed, where $B_1$ is the first block of elements, $B_2$ is the second block of elements and so on until $B_{32}$ is the $32^{nd}$ block of elements and $TB_n$ indicates transmission through the nth block of elements, and $RB_n$ means receiving on the nth block of elements:

$$TB_1,RB_1,TB_1,RB_2, \ldots ,TB_1,RB_n,TB_2,RB_1,TB_2,RB_2, \ldots TB_2,RB_n, \ldots ,TB_nRB_1, \ldots TB_nRB_n \quad (S1)$$

In a catheter designed to be introduced into cardiac arteries, space is at a great premium, and any design aspects that reduce the number of lines that must extend through the catheter yield a great benefit. Although a traditional multiplex device would permit any block 32 to be chosen at any time, this would require 5 control lines (yielding 32 combinations), not counting a transmit/receive choice line. Lowering the number of blocks to 16 would require blocks of 36—requiring four more coax signal lines 16, also difficult to fit into the catheter. To accommodate the above pattern of transmit and receive sequences, in one preferred embodiment control line 20b is a transmit line increment. In one preferred embodiment, chip 18 includes an incrementing register for transmit periods, incremented by a transmit increment line 20b and a separate incrementing register for receive periods, incremented by a receive increment line 20c. A transmit/receive selector line 20a thereby permits each to be incremented through its repeated cycles, as shown in sequence S1, listed above. In another embodiment, transmit/receive selector line 20a is used to increment the transmit and receive block registers, with for example, each rising edge counting as a transmit block increment and each falling edge counting as received block increments. A counter is placed in series with the transmit register so that only every 18th transition to transmit increments the transmit register and with every transition to receive incrementing the receive register, as indicated in sequence S1. This permits the transmit and receive increment lines to be eliminated. In yet another preferred embodiment, a single block increment line steps through the 18×18 (324) transmit/receive pairs sequence S1, which is then stored in the memory of the processor assembly (not shown).

Chip 18 is connected to array 30, by way of different techniques such as a flip chip bonding technique, pressure bonding through a thin layer of low viscosity adhesive (1-2 microns) or indium bonding. These are known techniques in the semiconductor/microchip industry. In the case of flip chip bonding, for example, a solder ball 40 is constructed on each chip contact 42, and then these solder balls are pressed into array 30, slightly crushing solder balls 40, to form a good bond, and to create robust electrical connections between each chip contact 42, and each element of array 30.

In this process, the thinness of chip 18 is a great advantage, because even though solder balls 40 have some thickness, the capability of chip 18 to bend slightly, due to its thinness, greatly facilitates the formation of a robust bond between solder balls 40 and each element of array 30. Adhesive filler is added among the thin solder balls to increase strength as well as conduct acoustic energy into the dissipative backing. In the case of pressure bonding electrical conductivity is achieved through the surface roughness of the bonded substrates, the high points of which penetrate enough through the thin layer of adhesive to assure electrical connection. In the case of indium boding conductive pads on both substrates (silicon chip 18 and flex circuit 44) are metalized with a one to three thousand angstroms of indium which then flows through the application of heat at a low temperature (about 170 C). In addition, chip 18 is approximately 10 μm thick thus effectively becoming an "anti-matching" layer and an integral part of the acoustic architecture as opposed to a thicker chip. Computer simulations indicate that the thickness of the silicon chip 18 can be further tweaked to achieve improved pulse properties.

The waveforms created by waveform generator 14 are typically two-cycle 35 MHz pulses, having pulse width of 5.7 nsec and pulse repetition frequency for 6 mm maximum penetration of 125 kHz or pulse repetition period of 8 usec. It should be noted that other frequencies in the range of 25 to 50 MHz may be utilized depending on resolution or penetration desired.

Referring, now, to FIGS. 4, 5, 6 and 7, in one preferred embodiment, multiplex chip 18 forms a portion of an imaging and ablation head 41 as described in detail in U.S. Pat. No. 8,702,609. The proximal side of multiplex chip 18 is attached to a central portion 43 (which may also be referred to as the "contact portion") of a flex circuit 44, having four arms 46, that are bent proximally and that each include a number of the signal coax cables 16, and for which at least one includes one or more control lines, such as lines 20A-D. Ultrasound absorbent backing material 48 is proximal to central portion 42. This material is a polymer or polymer blend chosen for its ability to absorb high frequency ultrasound and in particular, ultrasound in the range of 20-50 MHz. The lossy backing material has the same acoustic impedance as the flex circuit material, including the material of contact portion 43, to avoid reflection at the interface between the two. Proximal to backing material 48 is a radiopaque marker 50. After extending proximally past marker 50, flex circuit arms 46 are connected to a group of coax cables and other conductors, for signals to travel to a base station (not shown).

Figure 8:
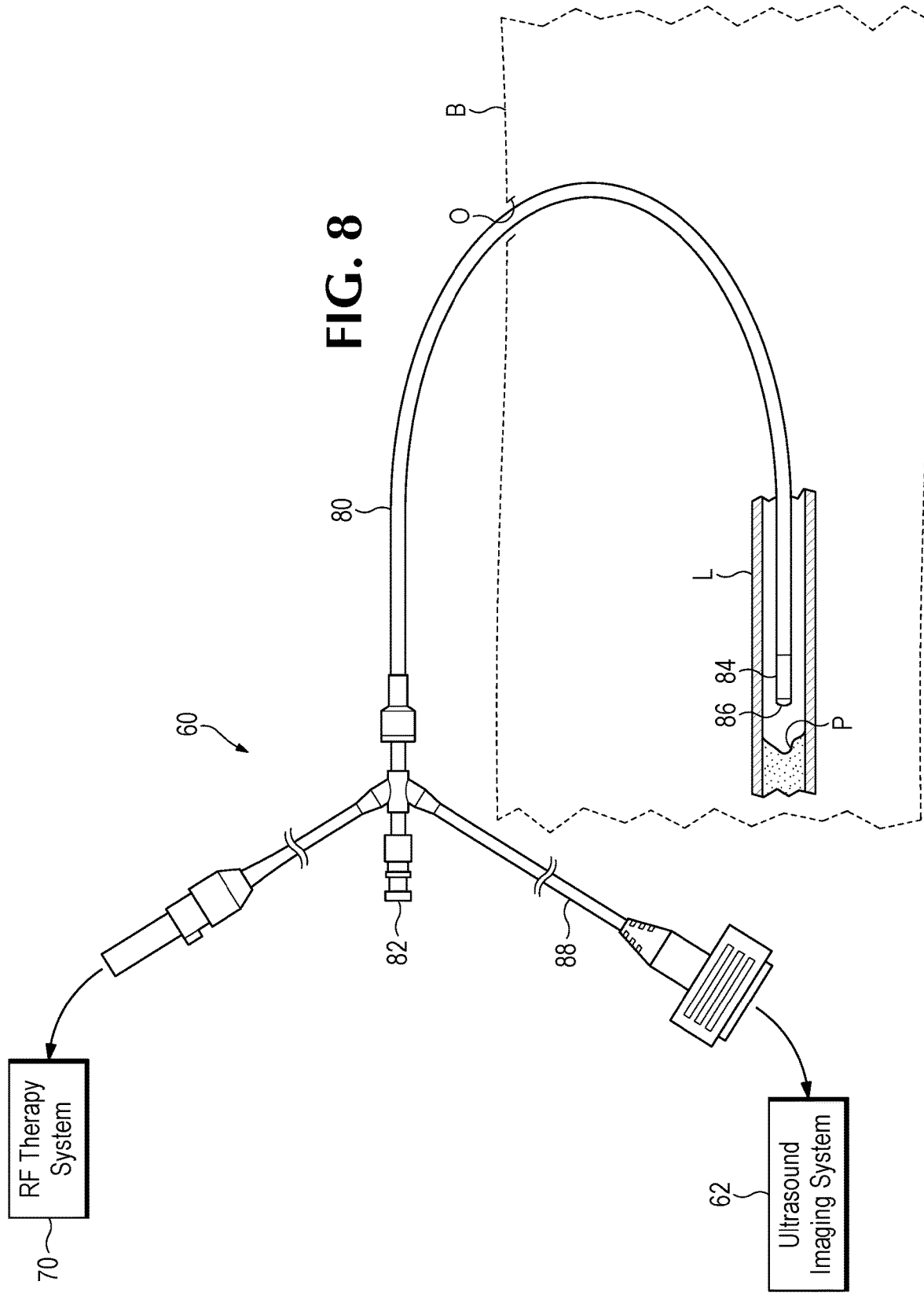
FIG. 8 is a diagram of a catheter configured for placement through an opening and into the body of a human patient or subject.

Referring to FIG. 8, in a preferred embodiment, ultrasound system 10 is physically implemented in a vascular imaging and plaque ablation catheter system 60. System 60 is arranged to provide images internal to body B for medical diagnosis and/or medical treatment. System 60 includes a control station comprising an ultrasound imaging system 62, of which processor assembly 12 and waveform generator and receive amplifier 14 form a portion, and an RF therapy system 70, each of which are operatively coupled to catheter 80, as well as appropriate operator input devices (e.g. keyboard and mouse or other pointing device of a standard variety) and operator display device (e.g. CRT, LCD, plasma screen, or OLED monitor).

Catheter 80 is configured for placement through opening O and into body B of a human patient or subject, as schematically represented in FIG. 8. Catheter 80 is preferably configured for insertion into a blood vessel or similar lumen L of the patient by any conventional vascular insertion technique. Catheter 80 includes a guide wire lumen that extends from a proximal port 82 through the distal tip 84 of the catheter 80, which is used to insert catheter 80 over a pre-inserted guidewire (not shown) via a conventional over the wire insertion technique. The guidewire exit port may be spaced proximally from the distal tip, accordingly, to known design. Catheter 80 may be configured with a shortened guidewire lumen so as to employ a monorail type insertion technique, or catheter 80 may be configured without any guidewire lumen and instead configured for insertion through the lumen of a pre-inserted guide catheter.

Figure 9:
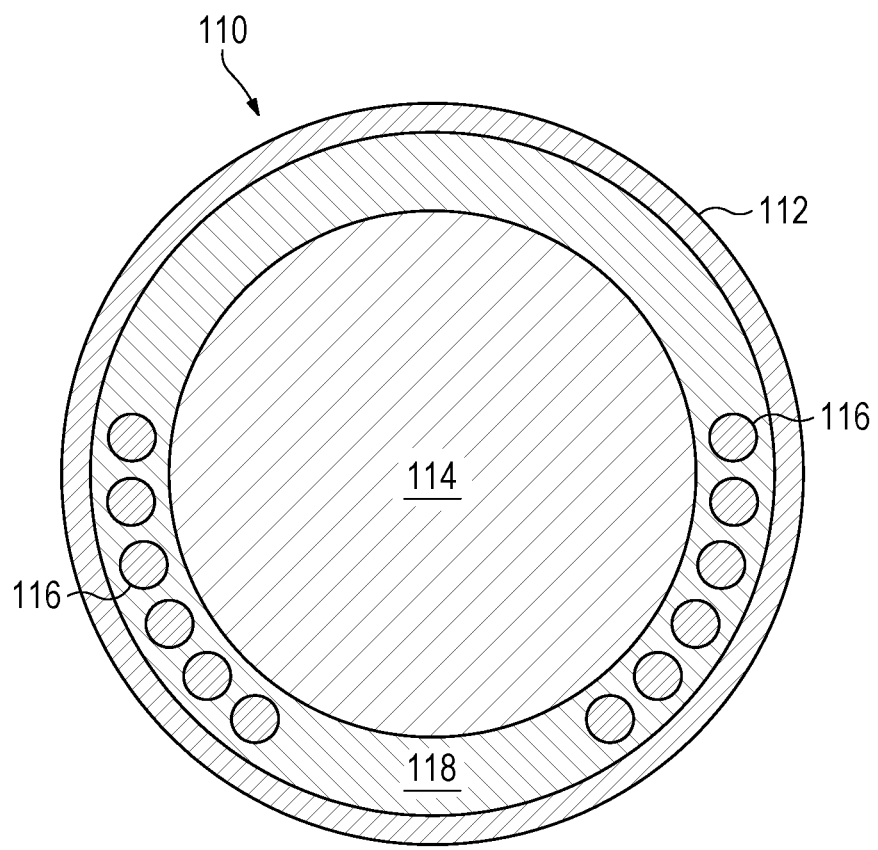
FIG. 9 is a cross-sectional view of a catheter in a Seldinger sheath.

Referring to FIG. 9, in one catheter embodiment 110, designed to be introduced into a blood vessel by of a sheath 112, according to the Seldinger method of catheter placement, a larger area lumen 114 is available for placement of coax cables, because the space for a guidewire is no longer necessary. RF and digital control wires 116 extend inside the side wall 118. In the Seldinger method a guidewire is used to facilitate the placement of the sheath 112. The guidewire is removed, and the sheath 112 is then used to guide the catheter 110. Because the space for the guidewire is eliminated, the number of coax cables may be increased, relative to an embodiment in which there is a space for a guidewire. There is an indication that with the embodiment of FIG. 8, 64 coaxial cables could be fit into the catheter, indicating that a 576 element array could be driven in 9 transmit/receive cycles.

Referring now to FIG. 8, the mux and amp chip 18 and ultrasound elements array 30 are located in distal end 84, whereas a set of RF ablation electrodes (not shown) form distal tip 86, which is designed to ablate arterial plaque P. Mini coax cables 16 extend through a side cable 88 and then through a lumen in catheter 80, together with control signal wires 20A-20D (which in one embodiment extend through the flexible exterior wall of catheter 80).

If the supporting tip surface is constructed of a suitable synthetic material capable of withstanding the high temperatures generated by the electrodes, the electrode material may be deposited or applied directly onto the tip. Suitable synthetic materials include high temperature plastics (e.g. Torlon, available from Solvay Advanced Polymers LLC, Alpharetta, Ga.) or silicone rubber materials (e.g. RTV325, Eager Plastics, Inc. Chicago, Ill., RTV 560 GE Plastics or SS-70 Silicone Rubber from Silicone Solutions, Cuyahoga Falls, Ohio). Another suitable material, TPX (4-polymethylpentene) is available from Mitsui Chemicals Inc., Tokyo, Japan. TPX is a solid plastic with acoustic properties similar to human tissue and therefore transports acoustic energy to tissue efficiently with little loss. The acoustic impedance of human tissue is about 1.55 MRayls while that of TPX is 1.78 MRayls (implying 93% transmission). TPX also has a relatively high softening temperature (about 350 F) and melting temperature of about 460 F, which makes it suitable for the ablation application, in which elevated temperatures may occur.

Figure 10:
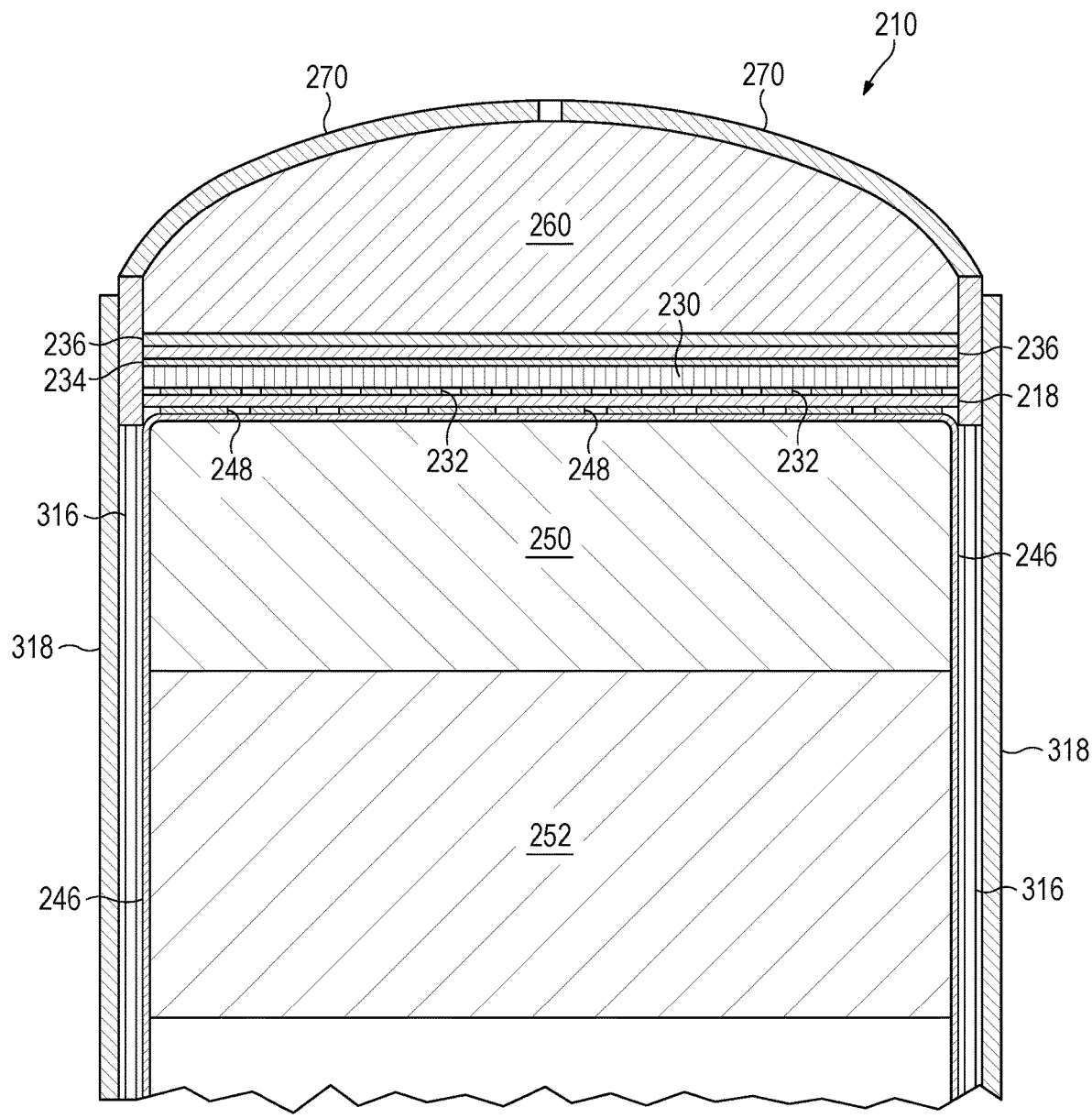
FIG. 10 is a sectional view of an alternative embodiment of a catheter end according to the present invention.

Referring to FIG. 10, in a further embodiment in the distal portion of an ablation catheter 210 an integrated circuit die (also known as chip) 218 drives an ultrasound array 230 by way of a set of contacts 232 (shown in a horizontally expanded form, for ease of presentation). A solid ground electrode 234 is immediately distal to the array 232, and immediately distal to electrode 232 are two stacked quarter wave matching layers 236. Chip 218 is controlled, powered and grounded by way of a flex circuit 246 through a set of contacts 248, similar in nature and function to contacts 17, 19, 21A-21D, 23 and 25 of FIG. 2. Backing material 250 is proximal to flex circuit 246, and a radio-opaque block 252 is proximal to material 250.

A sound lens 260 is distal to matching layers 236, and finally at the distal end, ablation electrodes 270 are available to ablate arterial plaque, when it is detected by the surgeon, using the ultrasound detection assembly (array 230 and supporting circuitry). RF electrodes are powered by RF wires 316, which, similar to wires 116 extend in the outer covering 318 of catheter 210.

Figure 11:
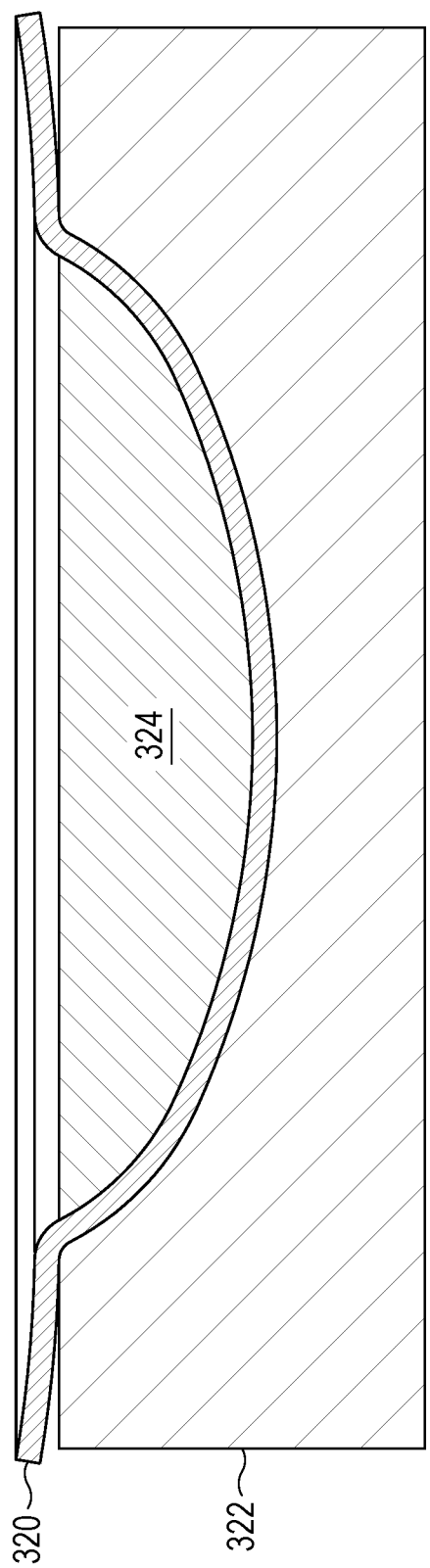
FIG. 11 is a sectional view of a lens and electrode work piece, in a mold.

In a preferred embodiment, electrodes 270 are made of titanium or a titanium alloy. In embodiments, electrodes 270 may be under 10 microns thick, under 8 microns thick, under 6 microns thick, under 4 microns thick, under 2 microns thick and under 1.5 microns thick. In a preferred embodiment, electrodes 270 are produced by sputter coating lens 260, which is rotated during sputtering to achieve a uniform coat of sputtered material. Referring to FIG. 11, in an alternative preferred method, foil 320 of electrode material is placed into a mold 322, in the shape of the final desired lens, and molten lens material 324 is poured on top of it and cured. Foil 320 may be of any of the thicknesses noted above and is typically about 1 to 2 microns thick and made of titanium or a titanium alloy. Titanium foil of these thicknesses is available from American Elements of Los Angeles, Calif.

After lens 324 is cured, the work piece comprising lens 324 and foil 320 is removed from the mold, strongly adhered to each other because no release agent is placed between the two. Foil layer is then laser machined to produce separate electrodes 270. The thin titanium electrodes 270 attenuate the ultrasound signal passing through them even less than the thicker electrodes previously disclosed.

As noted previously, suitable synthetic materials for lens 324 include high temperature plastics (e.g. Torlon, available from Solvay Advanced Polymers LLC, Alpharetta, Ga.) or silicone rubber materials (e.g. RTV325, Eager Plastics, Inc. Chicago, Ill., RTV 560 GE Plastics, or SS-70 Silicone Rubber from Silicone Solutions, Cuyahoga Falls, Ohio). Another suitable material, for lens 324 TPX (4-polymethylpentene) is available from Mitsui Chemicals Inc., Tokyo, Japan. TPX is a solid plastic with acoustic properties similar to human tissue and therefore transports acoustic energy to tissue efficiently with little loss. TPX also has a relatively high softening temperature (about 350 F) and melting temperature of about 460 F, which makes it suitable for the ablation application, in which elevated temperatures may occur.

In a preferred embodiment, chip 218 is less than a micron thick and is integrated with the polyimide film of the flex circuit 246, thereby reducing the overall size of the chip 218 and flex circuit in the acoustic stack, and reducing the acoustic effects, include impedance mismatch with the backing material and polyimide film of the flex circuit 246, to effectively become close to invisible. In one preferred embodiment the thickness of the combined flex circuit 246 central portion (underlying the chip 218) and chip 218 is only 30 microns. In a preferred embodiment chip 218 is about 0.2 microns thick. In an alternate preferred embodiment chip 218 is under 0.5 microns thick.

There may be instances where a surgeon prefers to have a faster frame update rate, even at the expense of image quality. Accordingly, in a preferred embodiment the surgeon can choose to use a sparse array scheme in the imaging optics to increase the frame rate of the images. The multiplexer feature of the IC chip 218 in the proximal end of the array enables the user to address a smaller subset of the array elements to increase the rate of acquisition of the images since each element is individually addressable, by the IC chip 218. This can be done through the user interface controls of the imaging system 10. Several geometries are possible, for example:

1. Remove every other element from the transmit/receive cycle (do not electronically drive). The aperture of the array and resolution will not change, however beam penetration, brightness and SNR will be reduced. This trade-off may be acceptable under certain circumstances in which the doctor will want more frequent update to the information provided by the images. More specifically, given 24 co-axial analog lines connecting the imaging system to the array and a 24×24 element array the use of every other element will result in effect in a 12×12 array. If all cross products are taken into account in the transmit/receive cycle then a straight forward calculation shows that the frame rate will increase by a factor of 16.
2. Remove every third element (16×16 element array). In this case the frame rate will increase by a factor of 5 and the image brightness will be better than case (3.i) above.
3. Remove every fourth element (18×18 element array) and rate will increase by a factor of 3.
4. Other element configurations are possible for different frame rates, including random selection of a fixed number of elements.

It may be noted that by decreasing the number of elements of element array 30, to the range of 200 to 400, it is possible to decrease the diameter of the catheter 80 to be in the range of 1.75-3.00 French (0.5-0.8 mm). This is suitable for insertion in smaller cranial blood vessels so that a system 10 can be used for treatment of brain related diseases. A set of higher frequencies than the version of system 10 used for coronary and peripheral artery disease (35-60 MHz range) and fewer analog transmit/receive lines in the catheter 80 (12-18 analog lines), are used in the version for treatment of cranial disorders. The intracranial applications include:

i. Plaque ablation in intracranial cerebrovascular arteries
ii. Pituitary tumors ablation
iii. Deep cortical tumor ablation
iv. Ablation of epileptic seizure nidus caused by gliotic scarring post stroke
v. Removal of obstructions in shunts for hydrocephalus condition While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An endoluminal catheter for providing image-guided therapy in a patient's vasculature comprising:
   (a) an elongated catheter body adapted to be inserted into a patient's vasculature, the catheter body defining a distal portion operable to be inside the patient's vasculature while a proximal portion is outside the patient;
   (b) a distal element including a sound lens having a distal surface and a set of electrodes adhered to said sound lens distal surface and forming a convex, generally round distal facing catheter face, defining a radial center, and bearing separately-controllable electrodes for performing controlled ablation of plaque in said patient's vasculature, each electrode extending away from said radial center in a direction different from the other electrodes;

(c) a distal facing array of ultrasound imaging transducers positioned in the catheter body proximal to the electrodes and configured to transmit and receive ultrasound pulses through said electrodes to provide real time imaging information of plaque to be ablated by the electrodes;

(d) whereby a catheter operator can form an image of plaque on an artery interior and in response selectively activate one or more electrodes to remove plaque along a first circumferential portion of an arterial wall, while avoiding activating an electrode along a circumferential portion of an arterial wall that does not bear plaque; and (i) wherein said electrodes are less than 10 microns thick.

2. The catheter of claim 1, wherein said electrodes are less than 6 microns thick.

3. The catheter of claim 1, wherein said electrodes are less than 2 microns thick.

4. The catheter of claim 1, wherein said electrodes are about 1 micron thick.

\* \* \* \* \*